(12) United States Patent
Maekawa et al.

(10) Patent No.: US 6,833,266 B2
(45) Date of Patent: Dec. 21, 2004

(54) **METHOD FOR CULTURING *AGARICUS* EDIBLE FUNGUS**

(75) Inventors: Takaaki Maekawa, Ibaraki (JP); Hiroko Isoda, Tsukuba (JP)

(73) Assignee: Tsukuba Biosystem, Ltd., Ibaraki (JP)

( * ) Notice: Subject to any disclaimer, the term of this patent is extended or adjusted under 35 U.S.C. 154(b) by 20 days.

(21) Appl. No.: 10/054,905

(22) Filed: Jan. 25, 2002

(65) Prior Publication Data

US 2003/0005488 A1 Jan. 2, 2003

(30) Foreign Application Priority Data

Jan. 26, 2001 (JP) .......................................... 2001-018505

(51) Int. Cl.$^7$ .......................... A01N 63/00; C12N 1/00; C12N 1/20
(52) U.S. Cl. ...................... 435/254.1; 424/93.5; 426/29; 435/256.8; 435/911
(58) Field of Search .......................... 424/93.5; 426/29; 435/254.1, 256.8, 911, 243

(56) References Cited

FOREIGN PATENT DOCUMENTS

WO       00/65029       11/2000

OTHER PUBLICATIONS

Guha et al. "Effect of different carbon compounds on the submerged prod. of Agarcius . . . " see abstract, 1972.*

* cited by examiner

*Primary Examiner*—David M. Naff
*Assistant Examiner*—Deborah K. Ware
(74) *Attorney, Agent, or Firm*—Wenderoth, Lind & Ponack, L.L.P.

(57) ABSTRACT

A mushroom fungus belonging to the order of *Agaricales,* is cultured with good efficiency by using a liquid culture medium in such a way as to prepare the *mycelia* separated from the culture medium such that the culturing liquid can be served for food use. A liquid culture medium containing 3 to 16 g/liter of sucrose and 1 to 6 g/liter of maltose as a carbon source and 0.3 to 1.2 g/liter of yeast extract as a nitrogen source is inoculated with *Agaricus mycelia* and culturing is conducted by blowing into the culture medium sterilized air of 20 to 90% of the oxygen concentration.

2 Claims, 1 Drawing Sheet

METHOD FOR CULTURING *AGARICUS* EDIBLE FUNGUS

BACKGROUND OF THE INVENTION

The present invention relates to a method for efficiently culturing fungous mycelia to be presented for food use.

It is well known that the mycelia of matsutake (*Trrcholoma matsutake*), shiitake (*Lentinus edodes*), mushroom (*Agaricus campestris*), honshimeji (*Lyophyllum aggregatum*), hatsutake (*Lactarius hatsudake*), enokitake (*Flammuline velutipes*), nameko (*Pholiota nameko*) and others belonging to the order of *Agaricales* are generally served for food use and the production method thereof includes the mycelium liquid culturing method.

While this liquid culturing method is conducted usually in a culturing medium containing 50 g/liter of sucrose, 10 g/liter of nitrate-type nitrogen, 5 g/liter of sodium phosphate, 2.5 g/liter of magnesium sulfate and 0.2 g/liter of iron sulfate in a stationary condition, such a method cannot be employed as a mass production method because, in addition to the low productivity, a large man power is required for the recovery of the mycelia and the efficiency for recovery is low.

Furthermore, it is essential in this method for food use to remove the culture medium which contains ingredients having adverse influences on human body such as nitrates.

Besides, there is known a solid culturing method by utilizing bagasse of sugarcane. This method, however, is defective because a complicated treatment must be undertaken for separation of the mycelia in addition to a long term of 2 to 3 months required for obtaining a sufficient amount of the mycelia. Moreover, contamination of the fungus is sometimes found in this method so that it is a difficult matter in utilization of the mycelia as a food to secure safety by preventing occurrence of mold poison and the like. Therefore, it is usual to grow mycelia by utilizing the solid culturing method followed by generation of fruiting bodies by means of a further temperature control, which are served usually as a food on the market but there remains a serious problem in respect of safety in order to be served as such for food use because fruiting bodies in general exhibit large absorption of poisonous metals contained in agricultural chemicals and culture medium as well as heavy accumulation thereof.

SUMMARY OF THE INVENTION

The present invention has been completed with an object to efficiently culture a fungus belonging to the order of *Agaricales* such as mushroom by using a liquid culture medium in such a way of production that the mycelia separated from the culture medium and the culture liquid as such can be served for food use.

The inventors continued extensive investigations on the liquid culturing method of fungi and, as a result, previously proposed a method in which a liquid culture medium containing sucrose or a sucrose-containing material as the carbon source is inoculated with a desired fungus to effect culturing with continued bubbling of a sterilized air containing oxygen in a high concentration [International Publication No. WO 00/65029 (published Nov. 20, 2000)] and, after further continued investigations, have arrived at a discovery that production of the mycelia can be greatly increased by the use of yeast extract as the nitrogen source in place of nitrates heretofore used. Further, they have separated the liquid culture medium containing the mycelia and the mycelia from the liquid culture medium and have discovered that the effective ingredients coming from the mycelia and contained in the culture medium and the mycelia can be served separately as such for food use leading to completion of the present invention on the base of this discovery.

Namely, the present invention provides a method for culturing an edible fungus characterized in that a liquid culture medium containing from 3 to 16 g/liter of sucrose and from 1 to 6 g/liter of maltose as the carbon source and from 0.3 to 1.2 g/liter of yeast extract as the nitrogen source is inoculated with an *Agaricus* mycelium and culturing is conducted under bubbling of sterilized air or oxygen-enriched air of an oxygen concentration of from 20 to 90%.

PRACTICING MODE OF THE INVENTION

Figure 1:
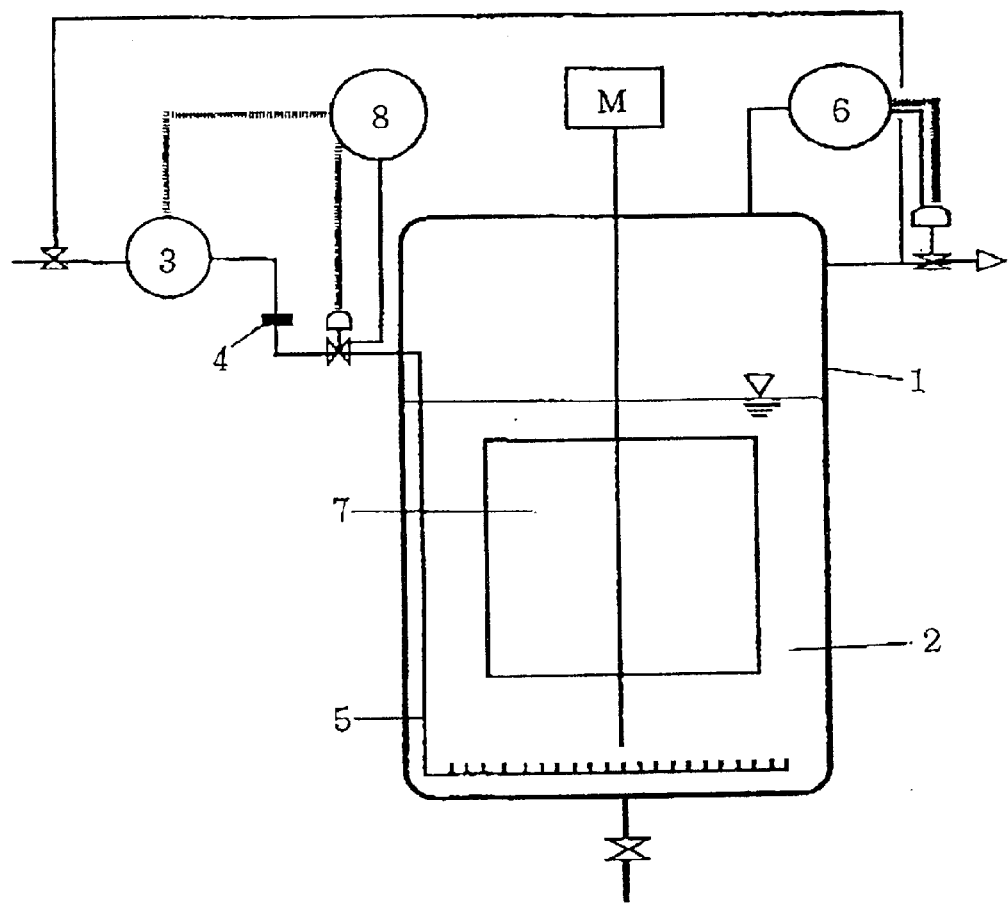
FIG. 1 is an apparatus system diagram including a schematic cross sectional illustration showing an example of the bioreactor suitable for practicing the method of the present invention.

In the method of the present invention, it is essential to employ a liquid culture medium which is characteristic in containing a combination of sucrose and maltose as the carbon source and yeast extract as the nitrogen source but, as to the other nutritive ingredients, the same ones as in conventional liquid culture media can be used. The yeast extract in this case also plays a role for the supply of a phosphate ingredient.

Namely, the liquid culture medium used in the method of the present invention is exemplified by an aqueous solution prepared by dissolving, in water, from 3 to 16 g of sucrose, from 1 to 6 g of maltose, from 0.3 to 1.2 g of yeast extract, from 0.4 to 0.7 g of sodium phosphate and from 0.25 to 0.35 g of magnesium sulfate per liter of the liquid culture medium.

And, when the above-mentioned sucrose is replaced partly or totally with a low-refined sugar, an effect is obtained that it serves as a supply source of mineral ingredients required in a liquid culture medium such as potassium and calcium. The compounding amount of such a low-refined sugar can be selected usually in the range from 10 to 70% by mass relative to the sucrose.

In the method of the present invention, the liquid culture medium of such a formulation is inoculated with from 1 to 10 mg/liter concentration as the dry mass of specified *Agaricus* mycelia followed by conducting culturing for 1 to 5 days while the temperature is maintained at 20 to 30° C. under bubbling of oxygen-enriched sterilized air of an oxygen concentration of 20 to 90% or, preferably, 60 to 80%. During this period, it is preferable that the agitation in the first stage is carried out at a low velocity with revolution of the stirrer of 10 to 50 rpm and thereafter agitation is conducted at an increased velocity to a revolution of 40 to 150 rpm. In this way, ball-like or polyhedral aggregates of the *Agaricus* mycelia having a diameter of 5 to 10 mm can be obtained.

When culturing in this case is conducted under normal pressure or under a condition of dissolved oxygen of 7 to 8 mg/liter, the aggregates as formed may have a blackened core portion presumably due to the fact that insufficient diffusion of oxygen to the core portion of the aggregate causes necrosis.

While, in the presence of a sufficient amount of the inorganic nutritive sources, the aggregates further grow to reach a size of 10 to 20 mm, the core portion becomes blackened with deficiency of the dissolved oxygen. On the other hand, no blackening is noted even when the diameter thereof has reached 40 mm if the amount of the dissolved oxygen in the liquid culture medium is increased to 15 to 30 mg/liter.

In the method of the present invention, it is optional that minced chips of at least one kind selected from agricultural by-products are used in combination with the sucrose as the carbon source. The agricultural by-product is crushed and used in the form of fine chips passing 100 mesh or finer or, preferably, passing 200 mesh or finer. In this case, these fine chips can promote aggregation of the fungous body by serving as nuclei for the growth of the mycelium aggregates. The agricultural by-product here implied means a by-product left after recovery of the principal object of the agricultural product including stalks and leaves of sugarcane, rice, wheat, corncob and Indian corn and processing residues of agricultural products such as wheat bran, rice bran and bagasse as well as wood flours.

Further, it is advantageous to use crude sugar as the sucrose because the impurities therein serve to stabilize the aggregates by increasing the affinity of the mycelia.

An adequate formulation of the liquid culture medium for the case of combined use of an agricultural by-product with the sucrose includes, per liter of the liquid culture medium, from 3 to 16 g of sucrose, from 1 to 6 g of maltose, from 0.1 to 15 g (dried amount) of comminuted material of the agricultural by-product, from 0.3 to 1.2 g of yeast extract, 0.4 g of sodium phosphate and 0.25 g of magnesium sulfate.

When a plant body of sugarcane, bagasse thereof or wheat bran is used in this case as the agricultural by-product, aggregation of the *Agaricus* mycelia is accompanied by very strong bitterness and generation of foams with unpleasant odor while such a phenomenon is rarely noted in the use of other agricultural by-products.

The size of the aggregates obtained in the method of the present invention depends on the concentration of the nitrogen source in the culture medium and is decreased by increasing the nitrogen concentration. On the other hand, the growth rate of the aggregates is strongly influenced by the types of the carbon source. For example, presence of sugarcane or bagasse thereof or wheat bran efficiently acts on the initial growth of the mycelia to cause rapid proceeding of aggregation so that adequate control of the dissolved oxygen is required in the beginning stage of culturing by adjusting the oxygen concentration in the air and the velocity of agitation.

The method of the present invention can be conducted, for example, in an apparatus shown in FIG. 1.

In FIG. 1, air is blown into the liquid culture medium 2 to fill the reactor body 1 consisting of a pressurizable vessel by way of the blowing pipe 5 from an air compressor 3 after passing a sterilizing filter 4 and culturing of the *Agaricus* fungus is conducted therein. During the while, the pressure of the air compressor 3 is increased, for example, to 0.1 to 0.5 MPa so as to gradually increase the dissolved oxygen concentration while the gas inside is discharged out of the system under control of the pressure of the discharged gas by means of the pressure-regulator 6 for discharge. During the while, agitation is conducted at a low velocity by means of the stirrer 7 driven by the motor M at the uppermost part so that ball-like or polyhedral aggregates are formed under the action of the liquid flow along the surface of the liquid culture medium 2 and the upward flow of air by the air blowing pipe 5.

A part of the air introduced into the above mentioned blowing pipe 5 is circulated through a pressure regulator 8 after branching according to need.

In this reactor, a real volume of the aggregates having reached 30 to 35% of the reactor volume corresponds to 60 to 70% of the apparent volume so that it is not advantageous to cause a decrease of the real volume by excessively increasing the diameter of the aggregates.

According to the present invention, *Agaricus* mycelia can be cultured by using a liquid culture medium not containing any toxic substances against human body such as nitrates so that the fungous bodies thus obtained are suitable for food use together with the useful ingredients in the liquid leading to a possibility of utilizing 3 to 4 times amount of useful ingredients as compared with conventional methods.

In the following, the present invention is described in more detail by way of Examples.

EXAMPLE 1

By using a bioreactor having an effective volume of 3 liters as the pressurizable vessel having a structure as shown in FIG. 1, 1 liter of a liquid culture medium containing 4 g/liter of crude sugar, 3 g/liter of brown sugar, 4 g/liter of maltose, 0.6 g/liter of yeast extract, 0.4 g/liter of sodium phosphate and 0.25 g/liter of magnesium sulfate was introduced thereinto and inoculated with 3 mg (dry weight) of Mushroom *Agaricus Blazei* Murill to conduct culturing for 3 days at a temperature of 30° C. so that 8.2 g (dry weight) of aggregate mycelia could be recovered. Besides, 250 mg of β-1,6-D-glucan could be recovered from the liquid.

In this case, the air pressure was 0.12 MPa and the flow rate of the air was 0.05 liter/minute.

EXAMPLE 2

In place of the liquid culture medium used in Example 1, 1 liter of a liquid culture medium containing 4 g/liter of crude sugar, 3 g/liter of brown sugar, 0.1 g/liter of a dry powder of sugarcane stalks and leaves (passing 200 mesh screen), 1.0 g/liter of yeast extract and 0.25 g/liter of magnesium sulfate was used and inoculated with 3 mg (dried amount) of Mushroom *Agaricus Blazei* Murill followed by culturing in the same manner as in Example 1. After culturing for 3 days, 11.2 g (dry amount) of mycelia and 350 mg of β-1,6-D-glucan in the liquid were obtained.

What is claimed is:

1. A method for culturing an edible fungus comprising providing a liquid culture medium containing 3 to 16 g/liter of sucrose and 1 to 6 g/liter of maltose as a carbon source and 0.3 to 1.2 g/liter of yeast extract as a nitrogen source incolating the medium with an *Agaricus mycelium,* and wherein said *Agaricus mycelium* while blowing into said medium sterilized air having an oxygen concentration of 20 to 90%.

2. The culturing method of an edible fungus described in claim 1 in which at least a part of the sucrose is a low-refined sugar.

* * * * *